United States Patent [19]

Badewien

[11] Patent Number: 4,566,451

[45] Date of Patent: Jan. 28, 1986

[54] VAPOR INHALATION DEVICE

[75] Inventor: Reinhard Badewien, Veenhusen, Fed. Rep. of Germany

[73] Assignee: Plantorgan Werk Heinrich G.E. Christensen KG, Fed. Rep. of Germany

[21] Appl. No.: 510,233

[22] Filed: Jul. 1, 1983

[30] Foreign Application Priority Data

Jul. 2, 1982 [DE] Fed. Rep. of Germany ....... 3224849

[51] Int. Cl.⁴ ............................................ A61M 11/02
[52] U.S. Cl. .......................... 128/200.21; 128/200.22; 261/DIG. 65
[58] Field of Search ...................... 128/200.18, 200.21, 128/200.22, 203.28, 203.12, 203.16; 261/DIG. 65, 78 A; 239/307, 338, 370, 343, 419.3, 427.3, 427.5

[56] References Cited

U.S. PATENT DOCUMENTS

| | | | |
|---|---|---|---|
| 451,822 | 5/1891 | Henry | 128/203.16 |
| 560,507 | 5/1896 | Krumm | 239/338 |
| 638,481 | 12/1899 | Seltzer | 128/200.21 |
| 2,202,701 | 5/1940 | Lehmann | 239/338 |
| 2,840,417 | 6/1958 | Dorsak et al. | 128/200.21 |
| 3,010,910 | 11/1961 | Gauchard | 128/200.21 |
| 3,265,067 | 8/1966 | Ehlinger | 239/338 |
| 3,591,090 | 7/1971 | Carden | 239/338 |
| 3,658,059 | 4/1972 | Steil | 128/200.21 |
| 3,744,771 | 7/1973 | Deaton | 128/200.18 |
| 3,826,255 | 7/1974 | Havstad et al. | 128/200.21 |
| 4,098,290 | 7/1978 | Glenn | 128/204.25 |
| 4,251,033 | 2/1981 | Rich et al. | 128/200.18 |

Primary Examiner—Henry J. Recla
Attorney, Agent, or Firm—Steinberg & Raskin

[57] ABSTRACT

A vapor inhalation device includes a container for medicated liquid to be vaporized and a cover situated over the container which communicates with a breathing mask which is positionable over the mouth and/or nose of the user. An insert having discharge openings and an atomizing device is arranged such that the vaporization rate of the medicated liquid in the container is enhanced through the introduction of a gaseous medium under pressure.

2 Claims, 11 Drawing Figures

VAPOR INHALATION DEVICE

BACKGROUND OF THE INVENTION

The present invention relates to a vapor inhalation device comprising a container for medicated liquid to be vaporized and a cover situated over the container adapted to communicate with a breathing mask which is positionable over the mouth and/or nose of the user.

In vapor inhalation devices of the type described above, an active substance containing essential oils and/or other medications is combined with hot water in the container to form a medicated liquid. During therapy, the mouth and nose of the user are pressed firmly against the breathing mask so that the vapors rising from the heated medicated liquid can be inhaled. In most designs, the cover is substantially conical in shape and the breathing mask is provided at the narrow end thereof.

It has been found that while such conventional devices are extremely simple in construction, they do not always function in an optimal manner since the rate of vaporization of the active substance is a function of the temperature of the medicated liquid and decreases rapidly as the liquid cools. Thus, at the beginning of the therapy, the temperature of the medicated liquid is relatively high so that vapors are formed having a high concentration of the effective substances. However, these vapors must be inhaled slowly and carefully due to their high temperatures. The range of high temperatures which provide optimal conditions for the vaporization of the active substances and, therefore, for optimization of the therapeutic process, can therefore not be fully taken advantage of.

On the other hand, as the medicated liquid cools to a lower, median temperature range, a more comfortable inhalation of the vapors is possible. However, the concentration of the therapeutic substances in the inhaled vapor is diminished. The temperature range of the medicated liquid drops fairly quickly with continued therapy and, accordingly, the concentration of the therapeutic substances within the inhaled vapors also rapidly diminishes. A point is eventually reached where no active therapeutic substances are contained in the vapor being inhaled and the therapy is for this reason often terminated prematurely. This is despite the fact that active therapeutic substances are indeed contained in the medicated liquid in adequate quantities.

SUMMARY OF THE INVENTION

Accordingly, it is an object of the present invention to provide a new and improved vapor inhalation device wherein the medicated liquid is vaporized with a therapeutically effective concentration of active substances therein and that the most favorable temperature of use.

Briefly, in accordance with the present invention, this and other objects are attained by providing a vapor inhalation device wherein means are associated therewith for enhancing the rate of vaporization of the medicated liquid, such means including means for introducing a gaseous medium under pressure into the vapor inhalation device. During use, an intensified liberation of the actual effective substances is achieved. The arrangement of the invention is especially advantageous in the event that the normal vaporization, i.e., the vaporization rate which has not been influenced by the present invention, has already been reduced due to the cooling of the medicated liquid. Thus, when the temperature of the medicated liquid is reduced, the present invention in one embodiment provides an aeration thereof to cause intensive turbulence therein to facilitate a residual vaporization of the medicated liquid. In this manner the active substances added to the hot water are substantially completely utilized during use.

In one embodiment of the invention, the vaporization rate of the medicated liquid is preferably increased by providing conduit means in which gas discharge openings are formed and which are arranged in the container of the vapor inhalation device such that the discharge openings are situated below the surface level of the medicated liquid. A gaseous medium under pressure, such as compressed air, is injected through the conduit means, such as by a small electrical pump or by a simple manually operated bulb, to exit into the medicated liquid through the discharge openings to create turbulence and enhance the vaporization rate thereof.

In another preferred embodiment which can also be advantageously combined with the embodiment described above, atomizing means are provided which upon the injection of a gaseous medium under pressure draws in medicated liquid through an aspirator-type device to spray the atomized medicated liquid into the area of the container above the level of the surface of the medicated liquid. A baffle disc may be arranged in opposed relationship to the atomizing means so that the droplets of medicated liquid are not directly introduced into the breathing mask.

Preferably, the means for increasing the rate of vaporization of the medicated liquid, whether in the form of pressurized gas discharge openings situated below the surface level of the medicated liquid or in the form of atomizing means as described above, or in a combination of both, is preferably provided as a single insert which is introduced into the container and connected to a gas injection conduit. In this manner, existing conventional inhalation devices comprising a container and cover associated with a breathing mask can be modified to incorporate the features of the present invention.

In one preferred embodiment, the insert comprises a disc-shaped member having a ring-shaped channel formed therein extending around the circumference of the disc. Perforations are provided extending between the ring channel and a surface of the disc, one of the perforations being connected to the compressed gas injection conduit while the other perforations constitute the gas discharge openings.

The configuration and dimensions of the disc-shaped insert are preferably chosen to correspond to the configuration and dimensions of the interior of the container.

The provision of a ring-shaped channel as described above allows for a uniform aeration of the medicated liquid and, therefore, a uniform vaporization thereof through the gas discharge openings. It is understood, however, that the insert and channel formed therein can have a different configuration such, for example, as crossed arms wherein each arm has an aeration or gas discharge opening formed at its free end.

The ring-shaped channel is preferably formed as a recessed groove in the circumferentially extending edge surface of the disc-shaped insert. The groove is sealed to form the channel by means of an elastic sealing element such, for example, as an O-ring formed of elastic material and which tightly fits around the exterior or the channel. The use of an elastic O-ring makes it possible to fit the disc with a close fit within the container. This in turn results in the advantage that the depth at which the insert is immersed in the medicated liquid can be permanently set so that at lesser immersion depths the cooling of the medicated liquid by the relatively cool injected compressed gas will occur at a slower rate than it would at greater immersion depths.

In the case where the insert is also provided with atomizing means, a small second container is preferably provided which may be filled, for example, with a highly concentrated solution of medicated active substances such as oils, salts, etc. The second container can be arranged so as to be movable with respect to the atomizing means in a manner such that the liquid intake opening of the atomizing means will be situated in the interior of the second container so that only the concentrated solution contained therein will be atomized and sprayed into the area above the surface level of the medicated liquid. In the case where a baffle element is provided over the atomizing means, such baffle element is advantageously designed in a manner such that the liquid droplets after impinging against the baffle element will fall back into the container so that only the vaporized portion of the medicated liquid is inhaled. In this manner, a more complete utilization of the active substance and a correspondingly greater therapeutic effect is achieved. The atomizing means constitutes both an alternative as well as a possible additional provision for the aeration openings situated below the level of the medicated liquid. Thus, the atomizing means can be operated either by a separately controlled gas conduit or by a branch of the same gas conduit supplying the compressed gas to the immersed discharge openings.

If additional active substances are introduced into the small second container associated with the atomizing means described above, these can be admixed in the vapor rising from the medicated liquid as an aerosol by means of the atomizing jet. In this manner a relatively precise dosing of additional active substances can be achieved so that an optimal therapeutic effect is attained with the inhalation device.

In a particularly preferred embodiment, the atomizing means includes a plug or tubular member having a discharge opening situated over the surface level of the medicated liquid. A small second container is mounted so as to be longitudinally movable over the tubular member so that the liquid intake opening formed in the tubular member can be located either within the small second container or outside of it. This provides the advantage that the injection or intake opening of the atomizing jet can be fluidly communicated with the medicated liquid in the main container or may function to draw the active substance from within the smaller second container into the atomizing jet.

In another preferred embodiment of the vapor inhalation device of the present invention, the atomizing means comprises a tubular nipple having a substantially conical exterior surface in which one or more longitudinally extending grooves are formed extending from the top to the bottom of the nipple. A jacket in which a bore having a configuration complementary to that of the conical exterior surface of the tubular nipple is fitted over the latter so that the grooves form conduits between the jacket and the nipple which extend from the upper end of the nipple to its bottom at which point the jacket terminates, the jacket being somewhat shorter than the nipple. The conic nipple projects from the bottom of the small second container containing the medicated liquid so that intake openings for the medicated liquid are defined between the jacket and the bottom of the second container.

It is preferred that the conical nipple and the second container for the medicated liquid which surrounds it be formed as a unitary part of an insert which can be positioned within the main container and its cover by means of a friction fit. In addition, fluid-type connecting channels are provided in the insert which provide fluid communication between the connecting conduit in the interior of the conical nipple.

The jacket having the internal conical bore is preferably arranged centrally of a larger perforated plate on which an external jacket skirt is arranged.

An insert is arranged in association with the outer jacket skirt which is mounted on the larger perforated plate in which the baffle element is mounted by adjustable mounting means. This assembly which forms the atomizing means is then mounted in a friction fit within the cover of the vapor inhalation device.

In order to obtain a particularly effective vaporization, in accordance with another aspect of the invention, an auxiliary discharge opening is provided in the conduit for the gaseous medium. The auxiliary discharge opening is preferably located in a connector element in a manner so that it can be closed by a valve device or by placing the tip of the users finger over the opening. If the auxiliary discharge opening is closed during inhalation, then the medicated liquid is vaporized only during inhalation. The auxiliary discharge opening is opened during exhalation thus preventing a superfluous additional vaporization of the medicated liquid at that time.

The individual components forming the insert described above such, for example, as the construction of the ring-shaped channel, are advantageously designed for easy disassembly. This facilitates cleaning of the vapor inhalation device which of course is a matter of great importance in medical applications.

DESCRIPTION OF THE DRAWINGS

A more complete appreciation of the present invention and many of the attendant advantages thereof will be readily understood by reference to the following detailed description when considered in connection with the accompanying drawings in which:

FIG. 1 is a schematic side elevation view in partial cross section of a first preferred embodiment of a vapor inhalation device according to the present invention;

FIG. 2 is a top plan view of an insert member forming a component of the vapor inhalation device illustrated in FIG. 1;

FIG. 3 is a sectional view taken along line III—III of FIG. 2;

FIG. 4 is a sectional view of a connector element in which an auxiliary discharge opening is formed which may form a component of one of the embodiments of the vapor inhalation device of the present invention;

FIG. 5 is a side elevation view in section of a second embodiment of a vapor inhalation device in accordance with the present invention;

FIG. 6 is a longitudinal cross-sectional view of the insert forming a component of the embodiment illustrated in FIG. 5 and constituting a section view taken along line VI—VI of FIG. 7;

FIG. 7 is a top plan view of the insert illustrated in FIG. 6;

DESCRIPTION OF THE PREFERRED EMBODIMENTS

Figure 1:
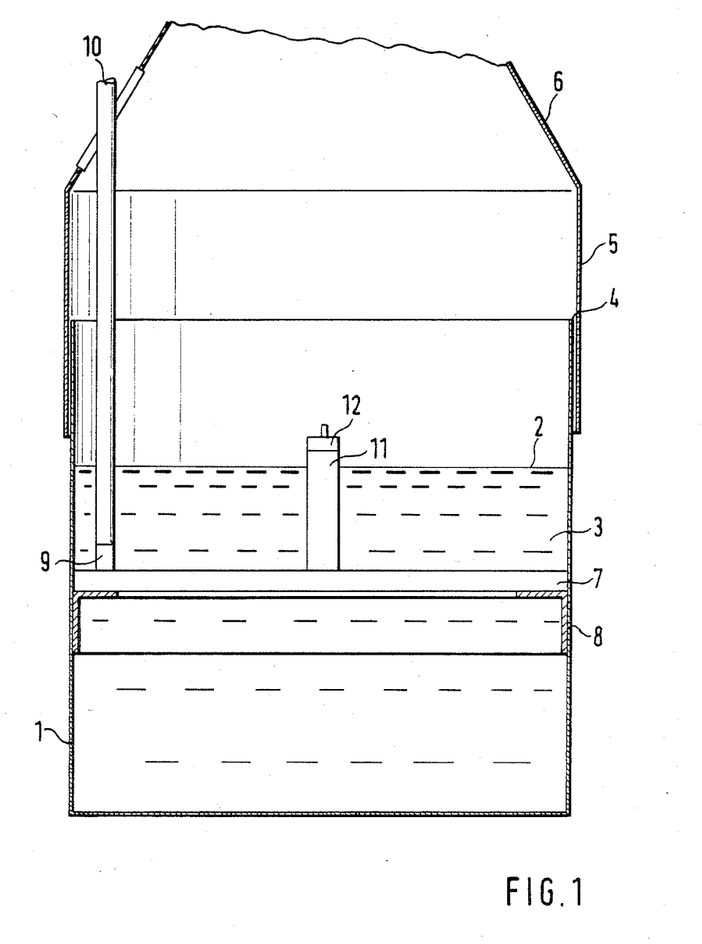
Figure 2:
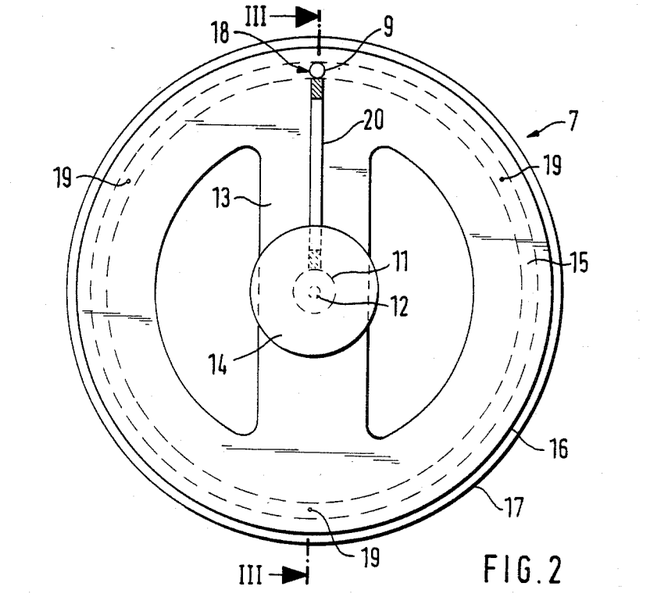
Figure 3:
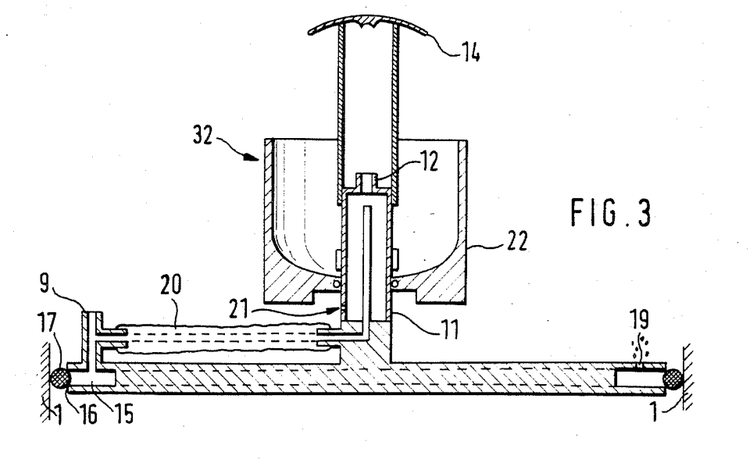

Referring now to the drawings wherein like reference characters designate identical or corresponding parts throughout the several views, and initially to the embodiment of the invention illustrated in FIGS. 1-3, the vapor inhalation device comprises a substantially cylindrical container 1 which is filled with a medicated liquid 3, the surface of the medicated liquid being designated 2. A cover 5, partially illustrated, is mounted over the upper edge 4 of the container 1. The cover 5 is provided with a conical wall section 6 having an opening (not shown) which is shaped in the form of a breathing mask which is positionable over one or both of the mouth and nose of the user. The container and cover of the vapor inhalation device are preferably formed of plastic material.

An insert 7 is arranged within the container 1 in a manner such that it lies below the surface 2 of the medicated liquid. The insert 7 is supported on a circular support shoulder 8 which projects inwardly from the interior wall of the container 1. The insert 7 is essentially plate-shaped and has one or more preferably uniformly spaced outlet or aeration openings formed in its upper surface, i.e., its surface facing the surface 2 of the medicated liquid. A gaseous medium, such as compressed air, is directed through an injection conduit 10 into appropriate conduit means, described below, formed in the insert 7 by means of a connector 9 so that the compressed air is discharged through the outlet or aeration openings into the medicated liquid.

A plug or tubular member 11 extends upwardly from a central region of the insert 7 so that its upper free end projects above the surface 2 of the medicated liquid. An atomizer jet nozzle 12 is provided at the free end of the tubular member 11. The atomizer jet nozzle 12 and tubular member 11 define a bore which fluidly communicates with the injection conduit 10 as described below.

Referring to FIG. 2, one construction of the insert 7 is illustrated. The insert 7 basically comprises a circular ring-shaped disc having a central diametrically extending cross bar 13 which supports the centrally arranged tubular member 11 on which the atomizer jet nozzle 12 is mounted. A curved baffle element 14 is arranged above the atomizer jet nozzle 12. A ring-shaped channel 15 is formed in the insert 7. The channel opens towards the exterior circumferential edge surface 16 of the disc-shaped insert 7, the open side of the groove being sealed by an O-ring 17 formed of flexible material to complete the channel. The supply end of the injection conduit 10 communicates with the channel 15 at a point designated 18 in FIG. 2. Gas discharge or aeration openings 19 are provided in the form of perforations extending between the channel 15 and the surface of the disc-shaped insert 7 which faces the surface of the medicated liquid so that compressed air will be discharged from the aeration openings 19 to aerate the medicated liquid in which the insert is immersed. At the same time compressed air is also forced through a length of tubing 20 forming a part of the conduit means so as to be directed into the tubular member 11 and atomizer jet nozzle 12. The tubing 20 branches off from the connector 9 by which the injection conduit 10 is connected into the ring-shaped channel 15.

Referring now to FIG. 3, a cross-sectional view through the insert 7 along line III—III is illustrated. As clearly indicated in FIG. 3, the insert 7 is held in place by means of a frictional engagement between the O-ring 17 and the inner wall of the container 1 so that in this manner the depth at which the insert is immersed within the medicated liquid can be easily adjusted.

Still referring to FIG. 3, the atomizing means, generally designated 32, including the tubular member 11 is clearly illustrated. An injection or liquid intake opening 21 is formed through the wall of the tubular element 11 through which the medicated liquid to be conducted to the atomizer jet nozzle 12 can be drawn in and entrained into the flow of the pressurized gaseous medium. The outer surface of the tubular member 11 also functions at the same time as a means on which a second bowl-shaped container or vessel 22 is mounted for movement along the length of the tubular member. The second container 22 can be filled with additonal specially medicated active substances.

In the form of the embodiment illustrated in FIG. 3, the second container 22 is shown in a position wherein it has been shifted closer to the free end of the tubular element 11 so that the injection opening 21 communicates with the medicated liquid within the main container 1 so that as compressed gaseous medium is introduced into the tubular element 11 and through the atomizer jet nozzle 12, such medicated liquid will be drawn through the intake opening 21 to be atomized and sprayed against the baffle element 14.

On the other hand, the small second container or vessel 22 can be shifted downwardly towards the base of the tubular element 11 until the injection opening 21 lies within the interior of the second container 22. When in this position, the active substances contained in the second container communicates with the intake opening 21 and is drawn into the gas jet to be atomized for spraying above the surface 2 of the medicated liquid within the main housing 1.

Figure 4:
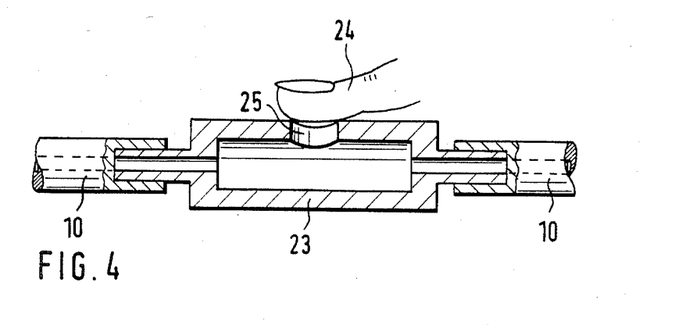

Referring to FIG. 4, an example of a connector element 23 is illustrated which can be inserted into the injection conduit 10 in order to interrupt the aeration and atomization when required as described below.

The connector element 23 is formed with a sealable auxiliary discharge opening 25 which can be closed by the user covering the same with his finger, designated 24. Pressurized air generated by a pump (not shown) can only flow into the injection conduit 10 if the auxiliary discharge opening 25 is sealed. Thus, when the auxiliary discharge opening 25 is opened, the air from the pump will escape through the opening 25 without reaching the connector 9 of the air injection conduit 10. Thus, by closing the auxiliary opening 25 during inhalation and freeing the opening during exhalation, an especially effective enhancement of the vaporization rate of the medicated liquid is achieved since vaporization will only be achieved when required, i.e., during inhalation, whereas when the effect of the injection of air into the medicated liquid will merely result in a cooling of the medicated liquid, such air injection is prevented.

Referring to FIGS. 5–11, another embodiment of a vapor inhalation device according to the present invention is illustrated which includes both a manually operated means for injecting compressed gas into the medicated liquid as well as atomizing means adapted to be connected another source of compressed gas which may be manually or motor operated.

Figure 5:
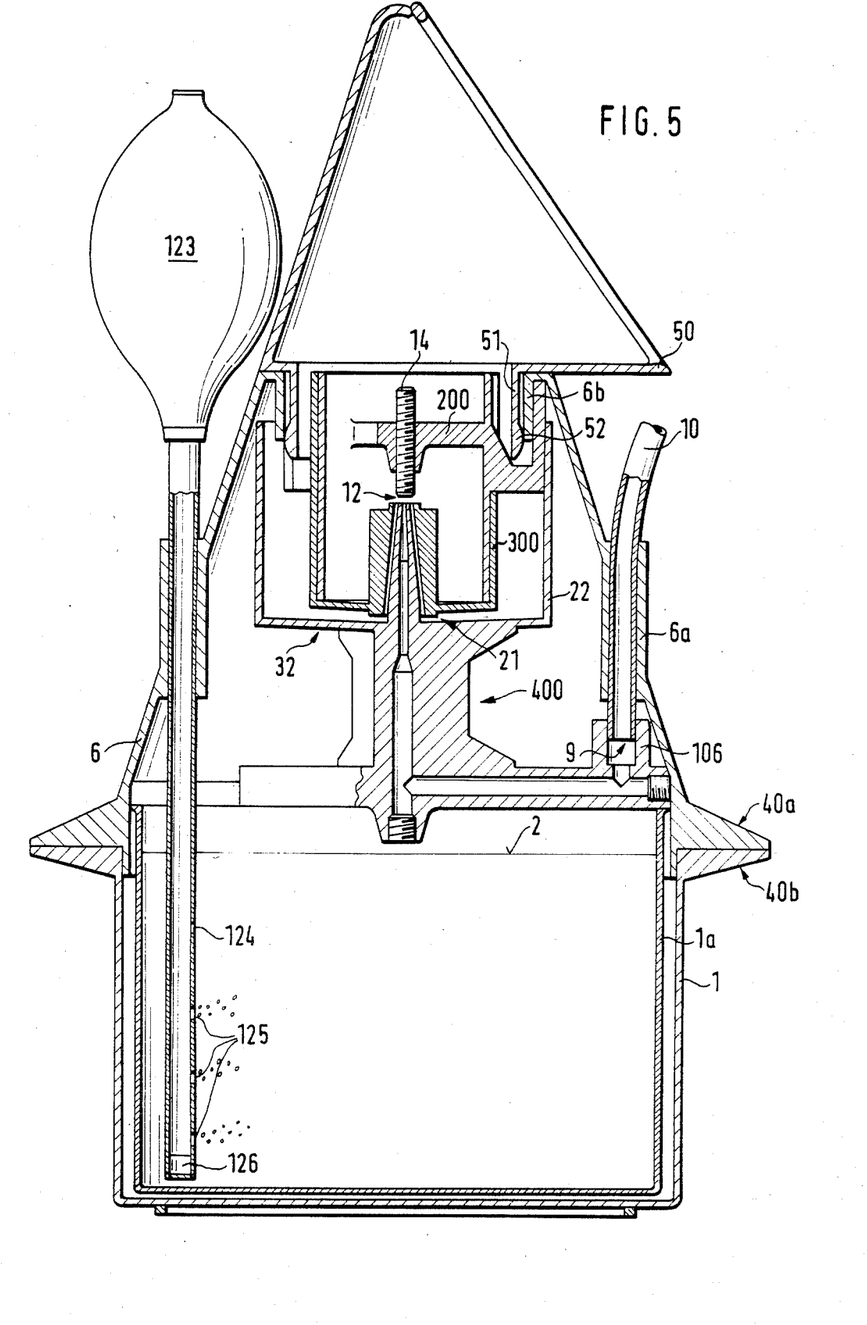

Referring to FIG. 5, the vapor inhalation device includes a substantially cylindrical container 1 having a pair of diametrically opposed handles 40b extending outwardly from the upper end thereof. A substantially conical cover 6 has a ring-shaped lip or projection at its lower end which tightly engages the upper end region of the interior of container 1 and is similarly provided with handles 40a which are alignable with handles 40b when the cover 6 is fastened to the container 1.

Conventional devices (not shown) are provided for connecting the cover 6 to the container 1 such, for example, as a bayonet type closure whereby the cover can be situated upon the container with a slight turning motion to firmly attach the two components. An interior container 1a is arranged within the main container 1, the exterior diameter of the interior container 1a being less than the interior diameter of the container 1. The interior container is supported by small projections or feet extending from its base so that in this manner the interior container is thermally insulated from the exterior container 1 by a layer of air. The conical cover 6 has a cylindrical socket portion 6b formed at its upper end. The socket 6b is defined by a portion of the wall of the cover which is turned inwardly to extend towards the container 1. Moreover, a pair of sleeve-type sockets 6a are arranged in the cover 6 to which conduit means extend to provide pressurized gas into the device as described below.

In this embodiment the breathing mask 50 is constructed separately from the cover 6 and has a substantially tetrahedral form wherein one of the surfaces of the tetrahedron is completely open. An opening is formed in one of the surfaces of the breathing mask 50 which is surrounded by an outwardly projecting cylindrical rim 51 which terminates at its outer edge in a bulge-shaped portion 52. The mask 50 is inserted into and held in the socket 6b through the frictional engagement of the bulge 52 with the socket 6b. With this arrangement, the mask 50 can be relatively easily twisted with respect to the cover 6 and can be somewhat tilted which substantially facilitates the use of the device.

A conduit 124 extends through one of the sleeve-type sockets 6a in the cover 6. A manually operated bulb or bellows 123 is fixed to one end of the conduit 124. The other end of the conduit 124 which terminates at a point slightly above the bottom of the inner container 1a is closed by a stopper 126. Small bores 125 are formed in the conduit 124 below the surface level 2 of the medicated liquid and constitute discharge openings for the pressurized air directed through the conduit 124 by manual operation of the bulb 123 which constitutes the source of pressurized air.

In the illustrated embodiment, the atomizing means 32 is situated within the cover 6 of the inhalation device, compressed air being injected into the atomizing device 32 by means of a conduit 10 which passes through one of the sleeve-type sockets 6a. The end 9 of conduit 10 is inserted into an air supply socket 106 of the atomizing means 32 while the other end of conduit 10 is connected to a suitably supply of compressed gas, such as compressed air.

The atomizing means constituting a component of the vapor inhalation device described above will now be described in greater detail referring to FIGS. 6–11.

Figure 6:
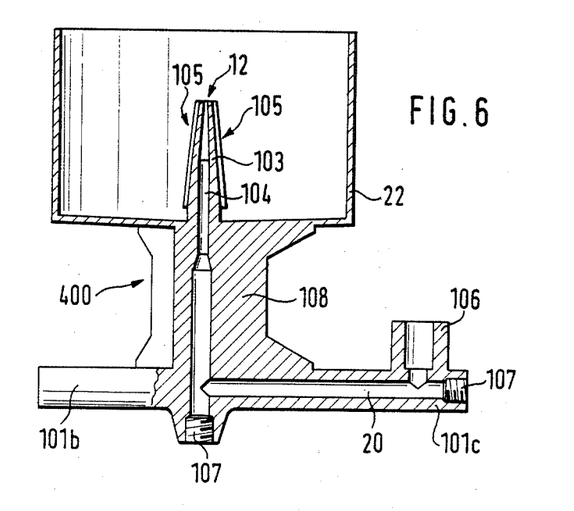
Figure 7:
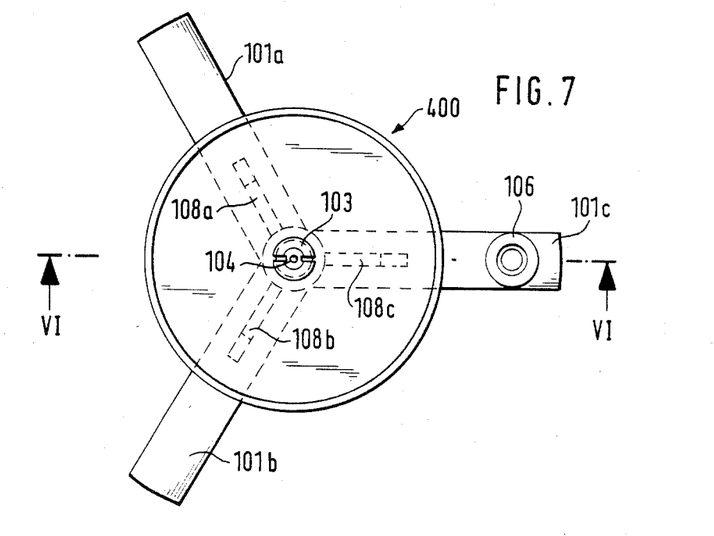

The atomizing means 32 includes as one of its components an insert 400 which is shown in an enlarged scale in FIGS. 6 and 7. Insert 400 is arranged in the cover 6 and is preferably constructed from plastic as a one-piece injected molded member including three arms 101a, 101b and 101c. One of the arms (e.g. arm 101c) has the supply socket or connection plug 106 formed thereon which is connected to the conduit 10 as seen in FIG. 5. The plug 106 is fluidly connected to a vertical channel 104 through a channel 20 which extends through the arm 101c. According to the illustrated embodiment, the various channels are bored in the insert 400 so that closure plugs 107 are provided at the blind ends of the channels to close the same. In the case where the insert 400 is formed of more than one piece, such as in a two-piece design, wherein the two half members are pressed against and adhere to each other, the closure plugs 107 are of course not required.

A spacer 108 comprising three vertically extending webs 108a, 108b and 108c, extends upwardly from the retaining arms 101 to support a substantially cylindrical second container 22 adapted to contain a suitable pharmaceutical preparation. A tubular pipe 103 having an axis aligned with the axis of the second container 22 projects upwardly from the bottom of the container with the pipe bore forming the vertical channel 104. The tubular pipe 103 has an upwardly tapering conical exterior surface in which a pair of grooves 105 are formed and which extend from a point proximate to the bottom of the tubular pipe 103 to its upper end.

Figure 8:
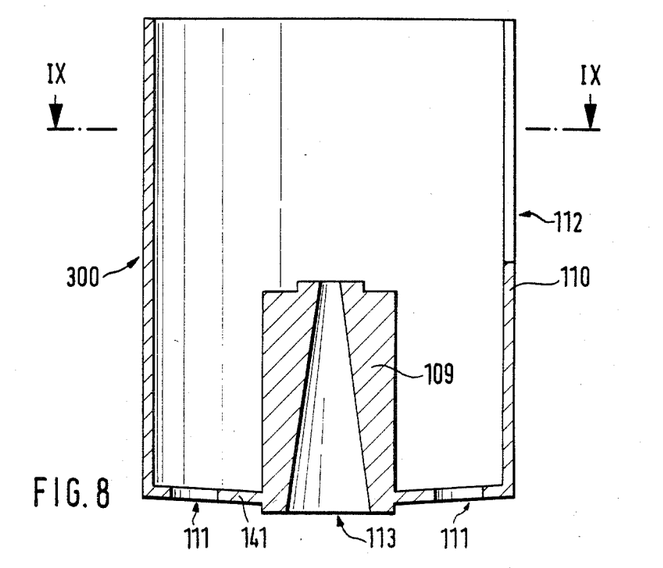
FIG. 8 is a longitudinal cross-sectional view of a component of the embodiment illustrated in FIG. 5 incorporating the jacket of the atomizing means and constituting a section view taken along line VIII—VIII of FIG. 9.
Figure 9:
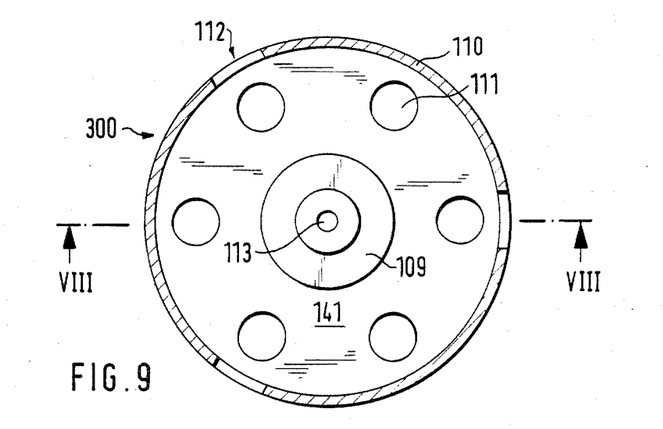
FIG. 9 is a sectional view taken along line IX—IX of FIG. 8.
Figure 10:
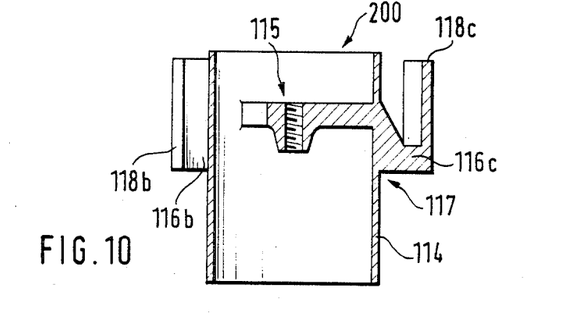
FIG. 10 is a longitudinal cross-sectional view of a component of the embodiment of the vapor inhalation device illustrated in FIG. 5 incorporating the baffle adjusting assembly, FIG. 10 constituting a section view taken along line X—X of FIG. 11.
Figure 11:
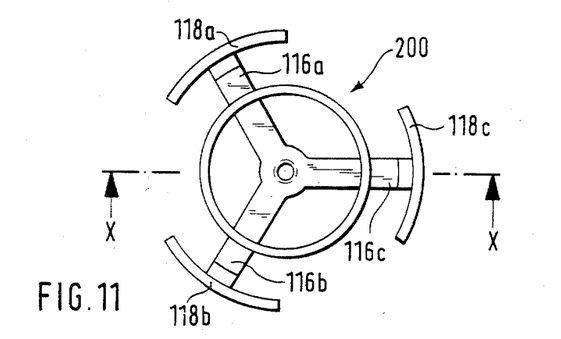
FIG. 11 is a top plan view of the baffle adjusting assembly component illustrated in FIG. 10.

As seen in FIG. 5, another component 300 is attached to the tubular pipe 103 of the insert 400, the component 300 being described in greater detail with reference to FIGS. 8 and 9. Component 300 includes a jacket 109 having a substantially cylindrical exterior surface and an interior substantially conical bore 113 having a shape which substantially corresponds to the conical outer shape of the tubular pipe 103. The length of the jacket 109 is such that after the jacket is fitted over the tubular pipe 103, the upper end of the jacket 109 is substantially flush with the upper end of the tubular pipe 103 while the lower end of the jacket 109 is situated somewhat above the bottom of the second container 22. In this manner, the grooves 105 formed in the conical tubular pipe 103 are formed into conduits or channels which open at both their top ends and at their bottom ends proximate to the bottom of the second container 22.

As soon as the second container 22 is filled with the active material to be atomized and compressed air is introduced into the channel 104 (through conduit 10, connector 106, and channel 20) the active liquid is drawn in through the conduit or channels 105 from the container 22 by the reduced pressure resulting from the rapid flow of the compressed gas at the outlet end of the channel 104. The active material is thereby aerated by the compressed air and thereby atomized. The outlet end of the channel 104 together with the grooves 105 thus form an atomizer jet nozzle 12.

As further seen in FIGS. 8 and 9, the jacket 109 is connected to a circular plate 141 which is preferably integral with a cylindrical external jacket skirt member 110 which surrounds the jacket 109. Openings 111 are formed in the circular plate 141 and the atomized liquid which is not inhaled is passed back into the second container 22 through the openings 111.

Referring to FIG. 5, a baffle element 14 is arranged over the atomizer jet nozzle 12. The baffle element 14 is mounted for adjustable movement in an insert, generally designated 200, illustrated in detail in FIGS. 10 and 11. The insert 200 includes an interiorly threaded tube 115 supported at the center of three radially extending arms 116*a*, 116*b* and 116*c*, the arms being themselves supported on a cylindrical sleeve 114. The arms 116*a*, 116*b* and 116*c* project outwardly of the sleeve 114 and terminate in cylindrical segments 118*a*, 118*b* and 118*c*. The adjustment insert 200 for the baffle element 14 is associated with the component 300 (FIG. 8) by providing that the sleeve 114 of insert 200 fit within the jacket skirt member 110 of the component 300 and so that the cylindrical segments 118*a*, 118*b* and 118*c* are positioned as shown in FIG. 5. It is noted that three slips 112 (FIGS. 8 and 9) are longitudinally formed in the jacket skirt member 110 to receive the radially extending arms 116 in assembly.

As seen in FIG. 5, the cylindrical segments 118*a*, 118*b* and 118*c* of the adjustment insert 200 are suitably dimensioned so that they surround and frictionally engage the socket 6*b* of the cover 6 to friction lock therewith. It is also seen in FIG. 5 that the ends of the arms 101*a*, 101*b* and 101*c* of the insert 400 are proximate to the region where interior surface of the cover 6 joins the lower cylindrical container section. This arrangement of the atomizing means 32 insures that the jet nozzle 12 is always correctly aligned with the baffle element 14 without requiring any special adjustment steps even after disassembly of the device. Additionally, this construction assures that the three components 200, 300, 400 can each be manufactured as a single piece from plastic without requiring larger expenses for secondary finishing steps and the like.

It is also preferred that the central region of the bottom of the second container 22 be slightly depressed as seen in FIG. 5 so that all of the liquid introduced into the container 22 for vaporization will reach the intake opening of the atomizing means defined at the bottom of the grooves 105 formed in tubular member 103.

The capability of adjusting the position of the baffle element 14 is advantageous in that the size of the droplets present during vaporization can be adjusted to meet specific requirements.

In a typical operation of the vapor inhalation device of the present invention, liquid at a temperature of 80° C. is introduced into the inner container and only the bellows or bulb 123 is operated. At a room temperature of 21° C., the inhaled vapor reaches a temperature of about 46° C. The resulting aerosol mixes with the air-vapor mixture in the mouthpiece of the device and is inhaled there at a relatively comfortable temperature. The container must be so dimensioned as to allow a good initial warming over a large liquid surface.

Of course, during the operation described above, the atomizing means 32 can be operated for further facilitating the rate of vaporization of the medicated liquid.

The vapor inhalation device disclosed herein can be operated in several different ways. Thus, it is possible to operate the device so as to only atomize the medicated liquid, such as through the operation of the atomizing means 32 without concurrent operation of the bellows 123, such atomization being possible both at lower and higher temperatures of the medicated liquid. It is also possible to operate the bellows 123 to inject compressed air into the medicated liquid to provide an aeration effect in addition to the atomizing described above, again either at low or high temperatures of the medicated liquid. The aeration effect can be performed without the atomizing means in operation. Finally, the device can be operated in a conventional manner without enhancing the rate of vaporization through the means of the present invention.

Of course, the features of the invention included in the embodiment of FIGS. 1–4 can be combined with those of the embodiment of FIGS. 5–11. For example, the same conduit can be used to direct compressed gas both to the discharge opening situated below the surface of the medicated liquid to enhance the rate of vaporization by aeration as well as to the atomizing means which enhances the rate of vaporization by atomization.

Obviously, numerous modifications and variations of the present invention are possible in the light of the above teachings. It is therefore to be understood that within the scope of the claims appended hereto, the invention may be practiced otherwise than as specifically disclosed herein.

What is claimed is:

1. In a vapor inhalation apparatus including a first container having first means for vaporizing medicated liquid therein and a cover mounted over said first container and having outlet means adapted to communicate with a breathing mask positionable over at least one of the mouth and nose of the user, the improvement comprising:

means associated with said apparatus for enchancing the rate of vaporization of medicated liquid therefrom including conduit means for introducing a gaseous medium under pressure into said apparatus, and second means within said apparatus for atomizing medicated liquid therein and directing it to said outlet means, said atomizing means being in fluid communication with said conduit means, said atomizing means including a first tubular member having a bore extending therethrough defining a discharge opening situated above the surface level of the medicated liquid in said first container, and a second tubular member cooperating with said first tubular member to define at least one liquid intake opening, said atomizing means further including a second container having an open upper end mounted on said first tubular member such that said liquid intake opening is adapted to communicate with the bottom interior of said second container, wherein said second container includes an upwardly axially extending tapered pipe constituting at least a part of said first tubular member, said tapered pipe having said bore formed therethrough and a substantially conical exterior surface in which at least one longitudinal groove is formed which terminates at an upper end of said pipe, said bore of said tapered pipe having one end terminating at the upper end of said pipe and an opposite end in fluid tight communication with said conduit means, wherein said second tubular member includes a jacket member disposed upon said tapered pipe and having a conical bore formed therethrough complementary with said conical exterior surface of said pipe, said tapered pipe being received in said conical jacket bore such that said at least one longitudinal groove forms a liquid conduit which terminates at the upper end of said pipe, the end of said liquid conduit proximate to the enlarged end of said tapered pipe constituting said liquid intake opening, whereby when gaseous medium is introduced through said conduit means into said first tubular member to discharge from said discharge opening, liquid situated within said second container is drawn through said at least one liquid intake opening to be atomized as the gaseous medium is discharged through said discharge opening, wherein said means for enhancing the vaporization rate of the medicated liquid further comprise baffle means arranged in opposed relationship to said discharge opening, further comprising a baffle component, and wherein said baffle means are adjustably mounted on said baffle component, an external jacket skirt member disposed around said jacket member, a base plate connected to and surrounding said jacket member and extending laterally therefrom, said external jacket skirt member being connected to said base plate, said base plate having openings formed therein communicating with the interior space within said external jacket skirt member and said baffle component being mounted on said external jacket skirt member, wherein said baffle means are mounted on said baffle component by a threaded connection and wherein said baffle component comprises a sleeve member fixed within said external jacket skirt member by a friction fit.

2. In a vapor inhalation apparatus including a first container having first means for vaporizing medicated liquid therein and a cover mounted over said first container and having outlet means adapted to communicate with a breathing mask positionable over at least one of the mouth and nose of the user, the improvement comprising:

means associated with said apparatus for enhancing the rate of vaporization of medicated liquid therefrom including conduit means for introducing a gaseous medium under pressure into said apparatus, and second means within said apparatus for atomizing medicated liquid therein and directing it to said outlet means, said atomizing means being in fluid communication with said conduit means, said atomizing means including a first tubular member having a bore extending therethrough defining a discharge opening situated above the surface level of the medicated liquid in said first container, and a second tubular member cooperating with said first tubular member to define at least one liquid intake opening, said atomizing means further including a second container having an open upper end mounted on said first tubular member such that said liquid intake opening is adapted to communicate with the bottom interior of said second container, wherein said second container includes an upwardly axially extending tapered pipe constituting at least a part of said first tubular member, said tapered pipe having said bore formed therethrough and a substantially conical exterior surface in which at least one longitudinal groove is formed which terminates at an upper end of said pipe, said bore of said tapered pipe having one end terminating at the upper end of said pipe and an opposite end in fluid tight communication with said conduit means, wherein said second tubular member includes a jacket member disposed upon said tapered pipe and having a conical bore formed therethrough complementary with said conical exterior surface of said pipe, said tapered pipe being received in said conical jacket bore such that said at least one longitudinal groove forms a liquid conduit which terminates at the upper end of said pipe, the end of said liquid conduit proximate to the enlarged end of said tapered pipe constituting said liquid intake opening, whereby when gaseous medium is introduced through said conduit means into said first tubular member to discharge from said discharge opening, liquid situated within said second container is drawn through said at least one liquid intake opening to be atomized as the gaseous medium is discharged through said discharge opening, wherein said means for enhancing the vaporization rate of the medicated liquid further comprise baffle means arranged in opposed relationship to said discharge opening, further comprising a baffle component, and wherein said baffle means are adjustably mounted on said baffle component, an external jacket skirt member disposed around said jacket member, a base plate connected to and surrounding said jacket member and extending laterally therefrom, said external jacket skirt member being connected to said base plate, said base plate having openings formed therein communicating with the interior space within said jacket skirt member and said baffle component being mounted on said external jacket skirt member, wherein said outlet means define an inwardly projecting tubular portion, wherein said baffle component further includes connecting means frictionally engaging said inwardly projecting tubular portion, wherein the mounting between said baffle component and said external jacket skirt member comprises a friction connection, and wherein said tapered pipe is received in said conical jacket bore with a friction fit, whereby said atomizing means are removable and adjustable with respect to said cover.

* * * * *